United States Patent [19]

Andrew

[11] Patent Number: 5,368,573

[45] Date of Patent: Nov. 29, 1994

[54] EPIDURAL NEEDLE HAVING CANNULA CLAMP

[76] Inventor: Daniel E. Andrew, 524 Beechwood Drive, Unit 34, Waterloo, Ontario, Canada, N2T 2G9

[21] Appl. No.: 133,261

[22] Filed: Oct. 7, 1993

Related U.S. Application Data

[63] Continuation of Ser. No. 829,633, Feb. 3, 1992, abandoned.

[51] Int. Cl.⁵ .............................................. A61M 5/178
[52] U.S. Cl. ...................................... 604/158; 604/272; 604/283
[58] Field of Search ............... 604/34, 51, 159, 161, 604/165, 178, 250, 272, 283, 905, 243, 249, 264, 158; 24/136 R, 115 M; 403/378, 379; 285/305; 128/DIG. 26; 81/487

[56] References Cited

U.S. PATENT DOCUMENTS

| | | | |
|---|---|---|---|
| 2,707,953 | 5/1955 | Ryan | 128/DIG. 26 |
| 3,682,173 | 8/1972 | Center | 604/159 |
| 4,209,015 | 6/1980 | Wicks | 128/DIG. 26 |
| 4,473,369 | 9/1984 | Lueders et al. | 604/250 |
| 4,541,657 | 9/1985 | Smyth | 285/305 |
| 4,632,436 | 12/1986 | Kimura | 285/305 |
| 4,689,043 | 8/1987 | Bisha | 604/249 |
| 4,973,312 | 11/1990 | Andrew | 604/165 |
| 5,000,614 | 3/1991 | Walker et al. | 403/379 |
| 5,105,807 | 4/1992 | Kahn et al. | 128/DIG. 6 |
| 5,137,517 | 8/1992 | Loney et al. | 24/136 |
| 5,158,569 | 10/1992 | Strickland et al. | 604/283 |

FOREIGN PATENT DOCUMENTS 0974024  11/1982  U.S.S.R. ............................ 285/305

*Primary Examiner*—C. Fred Rosenbaum
*Assistant Examiner*—Mark Bockelman
*Attorney, Agent, or Firm*—Arne I. Fors

[57] ABSTRACT

A clamping device is disclosed for securing a cannula in an epidural needle. The clamping device comprises a cylindrical housing seated in an epidural needle, the housing having a pair of diametrically opposed openings in which the arms of a clip are inserted to loosely receive the cannula or engage the cannula as desired.

8 Claims, 2 Drawing Sheets

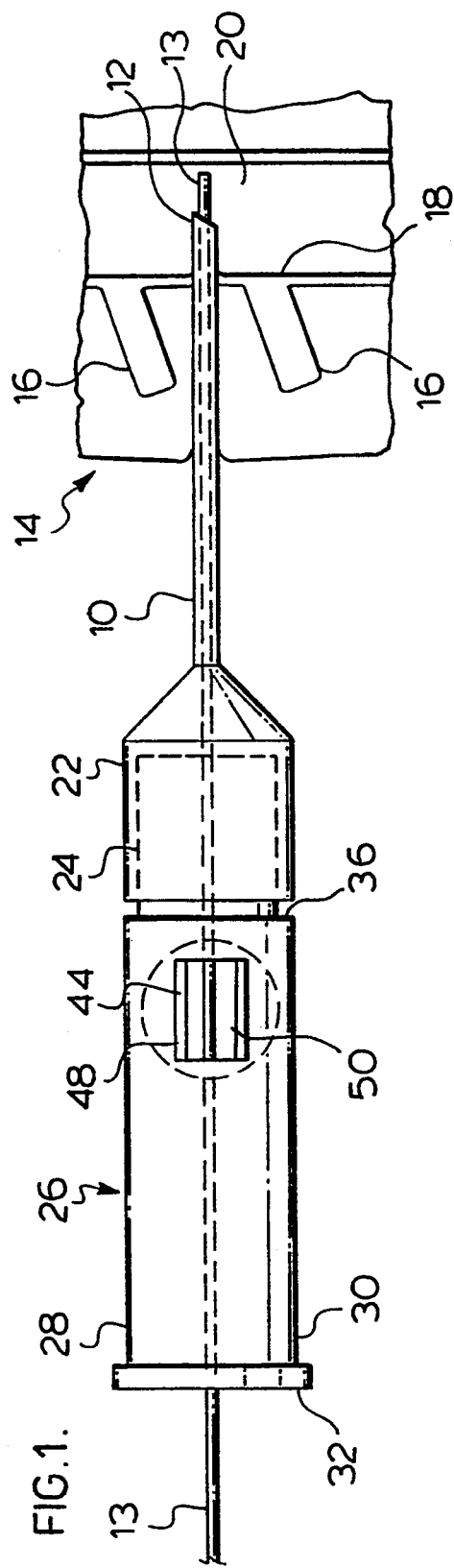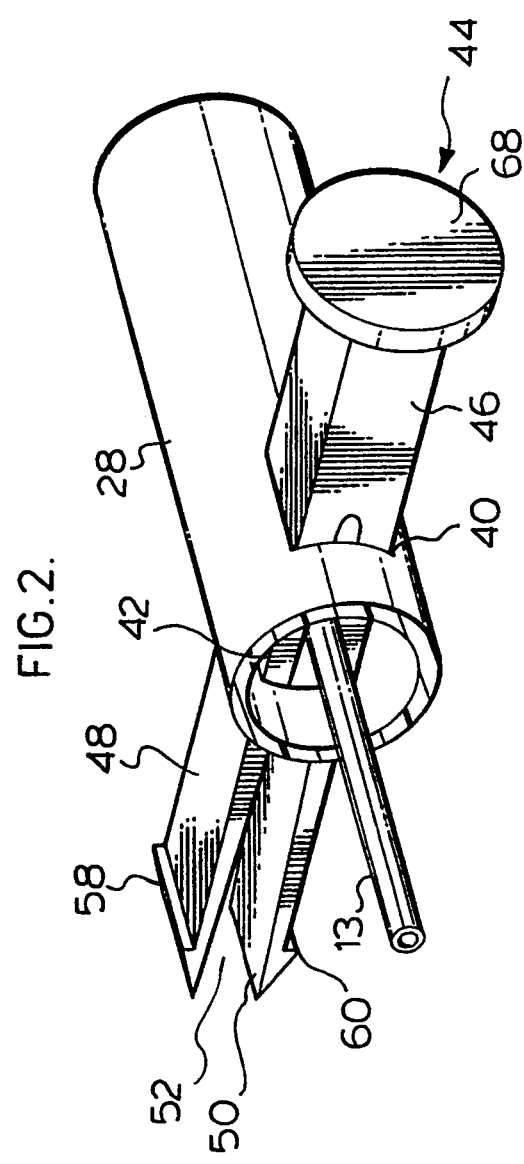

EPIDURAL NEEDLE HAVING CANNULA CLAMP

This application is a continuation of application Ser. No. 829,633, filed Feb. 3, 1992, now abandoned.

BACKGROUND OF THE INVENTION

This invention relates to the field of catheters and, more particularly, relates to a clamping device for locking a cannula in a housing.

U.S. Pat. No. 4,973,312 issued Nov. 27, 1990, discloses a system for the insertion of a flexible catheter through the epidural space and dura-arachnoid membrane into the subarachnoid space of a spine. The system comprises a hollow needle having a sharpened entry end for insertion into the epidural space and an exit end having a hub, a cannula with a distal end adapted for placement into and for axial movement within the hollow needle whereby said cannula can be advanced forwardly within the hollow needle for abutment of the distal end against the dura-arachnoid membrane to place tension on the dura-arachnoid membrane, and securing means adapted to be attached to the hub at the exit end of the hollow needle for locking the cannula within the hollow needle from axial movement.

It is a principal object of the present invention to provide a clamping device for securing the cannula to the epidural needle while the cannula exerts pressure on the dura.

BRIEF SUMMARY OF THE INVENTION

In accordance with the broad aspect of the invention, the clamping device for securing a tube such as a cannula to an epidural needle comprises an elongated hollow cylindrical housing for receiving said tube, said housing having a pair of diametrically opposed openings formed transversely therein, and a clip having a pair of opposed flexible arms joined at one end by a shank defining a tapered slot therebetween for insertion in snug-fitting relation through the openings formed in the housing whereby the tube is loosely received for sliding engagement between the opposed arms upon retraction of the clip within the housing and whereby the tube is gripped by the opposed arms upon extension of the clip within the housing.

BRIEF DESCRIPTION OF THE DRAWINGS

The clamping device of the invention will now be described with reference to the accompanying drawings, in which:

FIG. 1 is an elevation of an epidural needle with a cannula extending therethrough, secured by the clamping device of the invention, inserted into the epidural space of a spine;

FIG. 2 is a perspective view of the clamping device shown in FIG. 1, partly cut away, securing the cannula from axial movement;

DESCRIPTION OF THE PREFERRED EMBODIMENT

Figure 3:
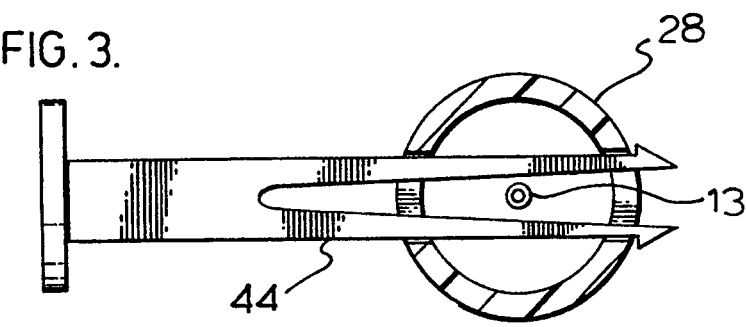
FIG. 3 is a section along line 3—3 of FIG. 2 showing the clip in a retracted position within the housing.

FIG. 1 of the drawings illustrates the placement of a hollow epidural needle 10 having a sharpened end 12 together with a cannula 13 extending therethrough and inserted into the back 14 of a patient between the spinous processes 16 of the vertebrae and through the ligamentum flavum 18 into the epidural space 20. The opposite end of needle 10 has a hub 22 having a conventional conical interior for receiving the forward tapered extension 24 of a clamping device 26 for securing the cannula from axial movement, to be described in detail with reference to FIGS. 2-6.

Clamping device housing 28 is an elongated cylindrical thin-walled hollow sleeve or housing preferably made of plastic having open end 30 with enlarged head 32 and opposite end with tapered extension 24 and shoulder 36. Extension 24 makes a snug friction fit with hub 22 of epidural needle 10. Cannula 13 passes loosely through housing 28 and needle 10 to extend into epidural space 20.

A pair of diametrically opposed transverse holes 40, 42 are formed in sleeve 28. Holes 40, 42 can be rectangular, e.g. elongated, square, or round or oval in shape. A clip 44 having a shank 46 and opposed spaced-apart arms 48, 50 extending axially from shank 46, formed from a flexible plastic, has a shape corresponding with the shape of holes 40, 42 for a snug sliding fit therein. Tapered slot 52 defined between arms 48, 50 has a width greater than the diameter of cannula 13 at the distal ends 54, 56 and a width less than the diameter of cannula 13 adjacent shank 46 for reasons which will become evident as the description proceeds.

The distal ends 54, 56 of arms 48, 50 preferably have pointed tips 58, 60 with a spacing less than the height of holes 40, 42 and outer barbs 58, 60 with a spacing greater than the height of openings 40, 42 to facilitate insertion of the clip 44 into holes 40, 42 and to restrain clip 44 from removal from housing 28.

Figure 4:
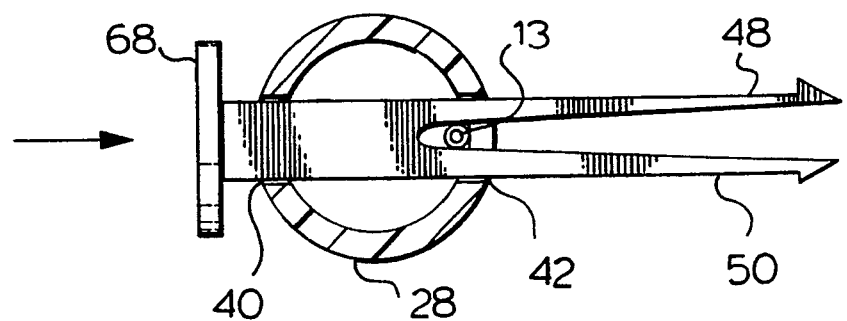
FIG. 4 is a section corresponding to FIG. 3 showing the clip in a fully extended cannula-engaging portion within the housing.
Figure 5:
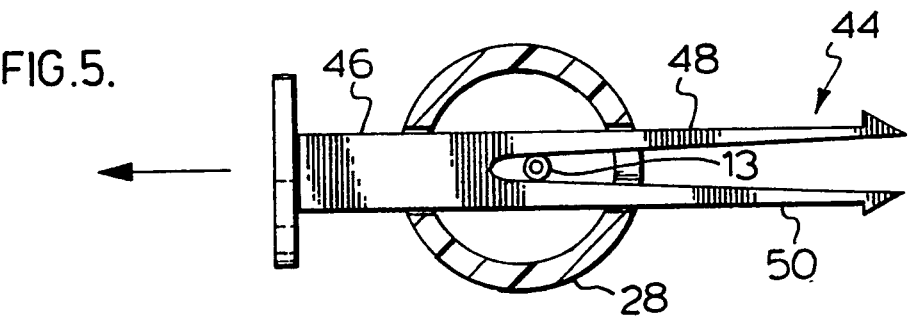
FIG. 5 is a section corresponding to FIG. 3 showing the clip in a partially retracted cannula-engaging position within the housing.
Figure 6:
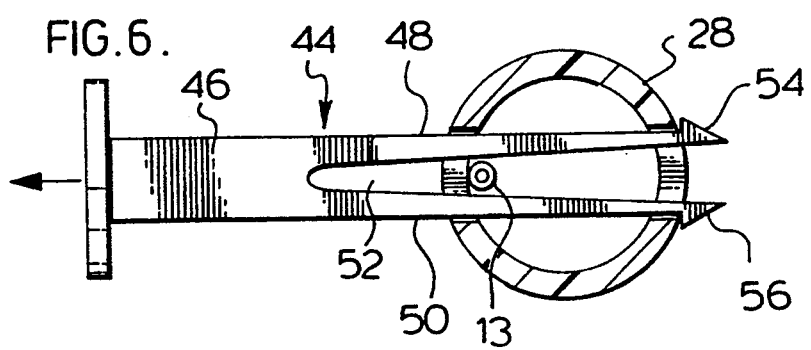
FIG. 6 is a section corresponding to FIG. 3 showing the clip in a retracted position which frees the cannula from the clip arms.

In operation, tubular cannula 13 which extends through epidural needle 10 between arms 48, 50 of clip 44, as shown in FIGS. 2 and 3, is extended into epidural space 20 for abutment against the dura-arachnoid membrane 62 to place the membrane 62 in tension, as described in U.S. Pat. No. 4,973,312, incorporated herein by reference. Clip 44 is then extended transversely through housing 28, as shown in FIG. 4, to push cannula 13 against the interior of housing 28 and to force the cannula towards the narrow end of slot 52 to pinch the cannula between arms 48, 50. Arms 48, 50 preferably are broad, i.e. sufficiently wide to avoid crushing the cannula. Clip 44 can then slide freely within housing 28 in holes 40, 42, as shown in FIG. 5, with cannula 13 securely gripped thereby to maintain a desired tension on membrane 62. When it is desired to release cannula 13, clip 44 is gripped by head 68 and retracted within housing 28 to the position shown in FIG. 6 whereby the cannula abuts the interior of housing 28 and is pulled free from the grip of arms 48, 50 adjacent shank 46.

It will be understood that modifications can be made in the embodiment of the invention illustrated and described herein without departing from the scope and purview of the invention as defined by the appended claims.

I claim:

1. A clamping device for frictionally securing a smooth surface cannula along its length without occluding said cannula for axial adjustment and for retaining the cannula in the hub of an epidural needle comprising: an epidural needle, an elongated open-ended, hollow cylindrical housing connected to the hub of the epidural needle for receiving said cannula axially therein, said housing having a housing wall with a pair of diametrically opposed openings fumed transversely therein, a clip having a pair of opposed flexible arms joined at one end by a shank defining a tapered slot therebetween inserted in snug-fitting relation through the openings formed in the housing wall perpendicular to the cannula within the housing whereby the cannula is loosely received for sliding engagement between the opposed arms or the clip upon retraction of the clip within the housing and whereby the cannula is frictionally gripped by the opposed arms upon extension of the clip within the housing, said clip shank having a head at one end with a diameter greater than the diameter of the holes and the opposed flexible arms having barbed tips at the distal cads thereof cooperating with the housing wall whereby the clip can move freely transversely within the housing between the said head and said barbed tips while being restrained from removal from the housing.

2. A clamping device as claimed in claim 1 wherein the tapered slot has a width adjacent to the clip shank less than the diameter of the cannula whereby the cannula is frictionally gripped between the opposed arms against the housing wall for securement of the cannula without occlusion of the cannula upon extension of the clip into the housing.

3. A clamping device as claimed in claim 2 wherein said hollow cylindrical housing has a tapered extension at one end for insertion into a hub of the epidural needle for a friction fit therein.

4. A clamping device as claimed in claim 3 wherein the barbed tips are pointed and the spacing of the points is less than the width of the holes to facilitate insertion of the arms into the holes and wherein the width of barbs is greater than the width of the holes to restrain the clip from withdrawal from the housing.

5. A clamping device as claimed in claim 1 wherein the clip is formed from a flexible plastic.

6. A clamping device as claimed in claim 5 wherein the clip has a rectangular cross-section.

7. A clamping device as claimed in claim 5 wherein the clip has a round cross-section.

8. A clamping device as claimed in claim 5 wherein the clip has an oval cross-section.

* * * * *